United States Patent
White et al.

(10) Patent No.: US 6,770,035 B2
(45) Date of Patent: *Aug. 3, 2004

(54) ULTRASOUND IMAGING GUIDEWIRE WITH STATIC CENTRAL CORE AND TIP

(75) Inventors: David A. White, San Jose, CA (US); W. Martin Belef, San Jose, CA (US)

(73) Assignee: Boston Scientific Corporation, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/405,586

(22) Filed: Apr. 1, 2003

(65) Prior Publication Data

US 2003/0195426 A1 Oct. 16, 2003

Related U.S. Application Data

(63) Continuation of application No. 09/844,644, filed on Apr. 27, 2001, now Pat. No. 6,585,654, which is a continuation of application No. 09/625,168, filed on Jul. 25, 2000, now Pat. No. 6,248,076, which is a continuation of application No. 09/393,507, filed on Sep. 10, 1999, now Pat. No. 6,171,250, which is a continuation of application No. 08/939,867, filed on Sep. 29, 1997, now Pat. No. 5,951,480.

(51) Int. Cl.$^7$ ................................................. A61B 8/14
(52) U.S. Cl. ...................................................... 600/463
(58) Field of Search ................................ 600/463, 466, 600/437, 585, 471, 485, 439

(56) References Cited

U.S. PATENT DOCUMENTS

| | | | | |
|---|---|---|---|---|
| 4,794,931 A | * | 1/1989 | Yock | 600/439 |
| 4,819,634 A | * | 4/1989 | Shiber | 606/159 |
| 4,936,307 A | | 6/1990 | Saito et al. | 600/463 |
| 4,951,677 A | * | 8/1990 | Crowley et al. | 600/463 |
| 4,961,433 A | * | 10/1990 | Christian | 600/585 |
| 4,979,939 A | * | 12/1990 | Shiber | 606/159 |
| 5,029,588 A | | 7/1991 | Yock et al. | 600/471 |
| 5,095,911 A | * | 3/1992 | Pomeranz | 600/463 |
| 5,178,159 A | | 1/1993 | Christian | 128/772 |
| 5,240,437 A | | 8/1993 | Christian | 439/668 |
| 5,243,988 A | | 9/1993 | Sieben et al. | 128/662.06 |
| 5,259,385 A | * | 11/1993 | Miller et al. | 600/453 |
| 5,304,115 A | * | 4/1994 | Pflueger, Russell et al. | 604/22 |
| 5,353,798 A | * | 10/1994 | Sieben | 600/462 |
| 5,368,035 A | * | 11/1994 | Hamm et al. | 600/466 |
| 5,372,144 A | | 12/1994 | Mortier et al. | 128/772 |
| 5,383,460 A | | 1/1995 | Jang et al. | 600/463 |
| 5,421,338 A | | 6/1995 | Crowley et al. | 128/662.06 |
| 5,438,997 A | | 8/1995 | Sieben et al. | 128/662.06 |
| 5,454,373 A | | 10/1995 | Koger et al. | 128/662.06 |
| 5,464,016 A | | 11/1995 | Nicholas et al. | 128/662.06 |
| 5,520,189 A | * | 5/1996 | Malinowski et al. | 600/466 |
| 5,546,947 A | | 8/1996 | Yagami et al. | 600/466 |
| 5,546,948 A | | 8/1996 | Hamm et al. | 128/662.06 |
| 5,582,171 A | | 12/1996 | Chornenky et al. | 128/653.1 |
| 5,660,180 A | | 8/1997 | Malinowski et al. | 128/660.03 |
| 5,738,100 A | | 4/1998 | Yagami et al. | 600/466 |
| 5,842,994 A | * | 12/1998 | TenHoff et al. | 600/466 |
| 5,951,480 A | * | 9/1999 | White et al. | 600/463 |
| 6,171,250 B1 | * | 1/2001 | White et al. | 600/463 |
| 6,248,076 B1 | * | 6/2001 | White et al. | 600/463 |
| 6,445,939 B1 | * | 9/2002 | Swanson et al. | 600/342 |
| 6,585,654 B2 | * | 7/2003 | White et al. | 600/463 |

* cited by examiner

*Primary Examiner*—Dennis W. Ruhl
*Assistant Examiner*—Ruby Jain
(74) *Attorney, Agent, or Firm*—Orrick, Herrington & Sutcliffe LLP

(57) ABSTRACT

An ultrasound imaging guidewire, that is inserted into a patient's body. The guidewire has a static central core and an imaging guidewire body comprising an acoustical scanning device. The acoustical scanning device can be rotated to obtain 360 degree acoustical images of a site of interest in the patients body. Furthermore, the imaging guidewire includes a connector that permits the imaging guidewire body to be disengaged from the static central core tip so that the imaging guidewire body can be axially translated to obtain multi-position imaging. The imaging guidewire body is axially translated without losing the original guidewire positioning because the static central core maintains its position in the patient's body.

37 Claims, 5 Drawing Sheets

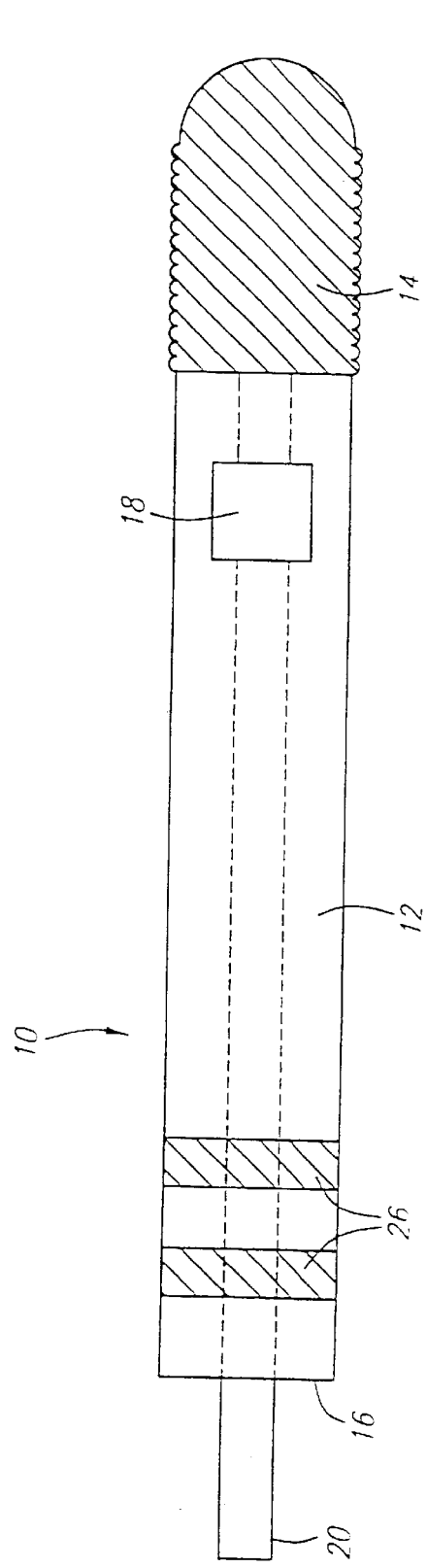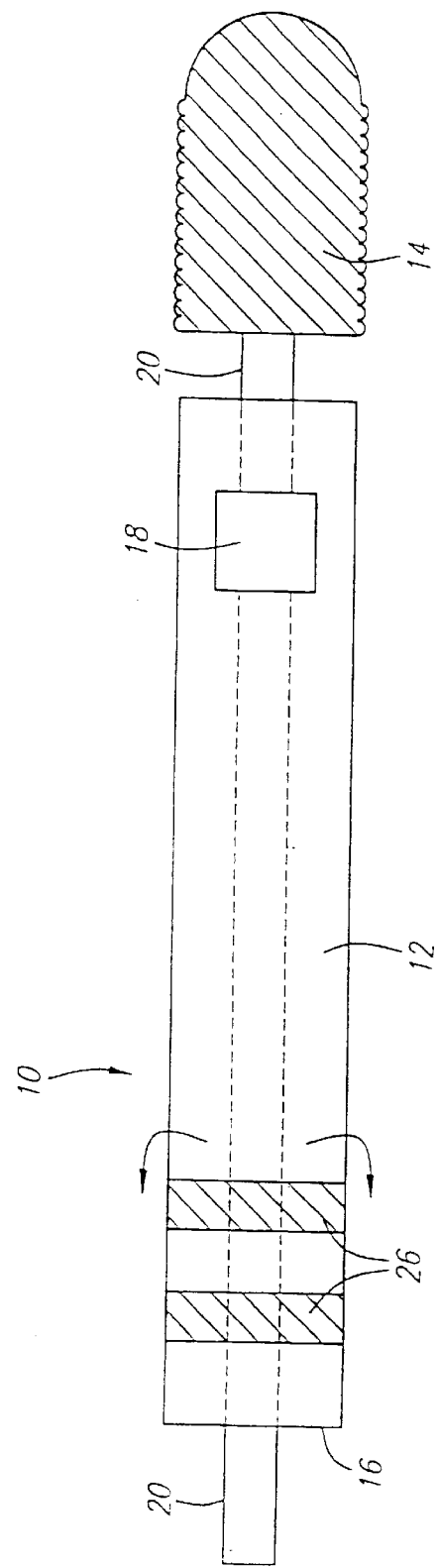

ULTRASOUND IMAGING GUIDEWIRE WITH STATIC CENTRAL CORE AND TIP

CROSS-REFERENCE TO RELATED APPLICATIONS

This application is a continuation of U.S. patent application Ser. No. 09/844,644, filed on Apr. 27, 2001 U.S. Pat. No. 6,585,654, which is a continuation of U.S. patent application Ser. No. 09/625,168 filed on Jul. 25, 2000 (now U.S. Pat. No. 6,248,076, issued Jun. 19, 2001), which is a continuation of U.S. patent application Ser. No. 09/393,507 filed on Sep. 10, 1999 (now U.S. Pat. No. 6,171,250, issued Jan. 9, 2001) which is a continuation of U.S. patent application Ser. No. 08/939,867 filed on Sep. 29, 1997 (now U.S. Pat. No. 5,951,480, issued Sep. 14, 1999).

FIELD OF THE-INVENTION

This invention relates to medical guidewires typically used by physicians to gain access to restricted regions of the body and over which therapeutic devices are passed for insertion to a site of interest. Specifically, the invention relates to an ultrasound imaging guidewire with a detachable imaging guidewire body and a stationary central core.

BACKGROUND OF THE INVENTION

Many surgeries involve the insertion of guidewires into a patient's body. The guidewire may be inserted into the digestive tract, urethra, blood vessels, heart chamber, a body cavity such as the abdominal cavity, or a hollow organ. Typically, an artery is the vessel of interest. The artery could be a relatively large peripheral vessel, a relatively small proximal coronary artery, or an artery of any size in between. The guidewire may include an imaging portion that permits close examination of the site of interest by means of ultrasonic waves. An ultrasonic imaging guidewire may permit the user to obtain 360 degree (i.e., cross-sectional) acoustic images of the vessel wall to, for example, determine the tissue morphology state of a site of interest, position a therapeutic device, monitor the progress of treatment or observe the site after treatment to determine the course of further treatment.

Often, the guidewire must be Positioned at a predetermined site after passing through a complex network of blood vessels. Such placement may require a considerable amount of time. Furthermore, the difficulty and time required for guidewire placement increases with increasing vessel occlusion at later stages of disease. Thus, placement of the guidewire can be a time-consuming and difficult task.

Accordingly, once the physician has taken the time to correctly place the guidewire, it is preferable to maintain the guidewire position. However, it is also desirable to obtain images of the diseased area which may require that the guidewire be axially translated to view the site of interest. Hence, after the physician places the guidewire, the physician needs to move the imaging guidewire back and forth to make a correct diagnosis of the lesion morphology. The problem with advancements and pullbacks of the imaging guidewire is that the physician may lose the correct placement of the guidewire, and have to spend additional time repositioning the guidewire. Thus, there currently exists a need to maintain guidewire positioning while permitting multi-position, real-time imaging.

Furthermore, the back-and-forth movement of the guidewire may damage the patient's vessels. Therefore, there currently exists a need to provide safer guidewire imaging.

A significant problem encountered by physicians is the proper positioning of stents. Stents are often used to prevent lumen closure following bypass surgery and to treat acute vessel closure after angioplasty. It is often extremely difficult for a physician to accurately determine the correct location to deploy a stent, particularly at a bifurcating vessel. Incorrect placement of a stent can lead to "stent jail" and is demonstrated in FIG. 3. As shown in FIG. 3, if the stent 100 is incorrectly placed at a bifurcating vessel location 102, the stent 100 may block the vessel 102 and the physician can no longer access that vessel 102. This is particularly dangerous if the vessel 102 becomes diseased, such as at 104, and access is needed for therapy. Thus, there currently exists a need for easier, multi-position, ultrasonic imaging of the site of interest to assist in accurate placement of a stent.

There also currently exists a need to provide improved imaging capabilities, without losing proper guidewire positioning, so as to efficiently locate the site of interest, to properly position therapeutic catheters such as an angioplasty balloon, and to observe continuously the site or sites of interest. There also exists a need to decrease the complexity and to save time associated with the ultrasonic imaging procedure.

SUMMARY OF THE INVENTION

Accordingly, a general object of the present invention is to provide an apparatus and method for permitting multi-position, ultrasonic imaging without losing correct guidewire positioning.

A further object of this invention is to provide a faster imaging guidewire procedure, and to eliminate the complexity associated with the ultrasonic imaging guidewire procedure.

Another object of this invention is to prevent harm to a patient's vessels by eliminating the back and forth movement of the guidewire tip.

In order to achieve the above objects of the present invention, an ultrasound imaging guidewire is provided with a connector to permit a static central core to be temporarily detached from an imaging guidewire body of a guidewire. A method is also provided to permit efficient and accurate imaging of the site of interest. The method includes the step of inserting a guidewire with an imaging guidewire body and a static central core into a patients body at a particular site of interest. Next, the imaging guidewire body is rotated at the site of interest to obtain acoustical images. Finally, the imaging guidewire body of the guidewire is axially translated to further obtain images of the site or sites of interest, without axially translating the static central core.

Additional objects, advantages, aspects and features of the present invention will further become apparent to persons skilled in the art from a study of the following description and drawings.

BRIEF DESCRIPTION OF THE DRAWINGS

FIG. 1A is an elevational view of an ultrasound imaging guidewire.

FIG. 1B is an elevational, view of the ultrasound imaging guidewire in a disengaged position.

DETAILED DESCRIPTION OF THE PREFERRED EMBODIMENT

Referring to FIGS. 1 and 2, the present invention is directed to an ultrasound imaging guidewire 10. The guidewire 10 must have sufficient pushability and torque transmission ability to traverse a tortuous anatomy of blood vessels. Pushability means the characteristics of the guidewire 10 that can reliably transmit a pushing force given by the operator at the proximal end of the guidewire to the distal end thereof. Torque transmission ability means the characteristics that can reliably transmit rotational force applied to the proximal end of the guidewire to the distal end thereof. The imaging guidewire body 12 exhibits uniform, suitable axial and lateral stiffness and torquability up to a desired distal region, where the stiffness gradually changes to a floppy tip 14. The guidewire enables predictable torquing and pushability from proximal regions to the distal floppy tip 14 as is required for proper functioning as a guidewire.

Figure 7:
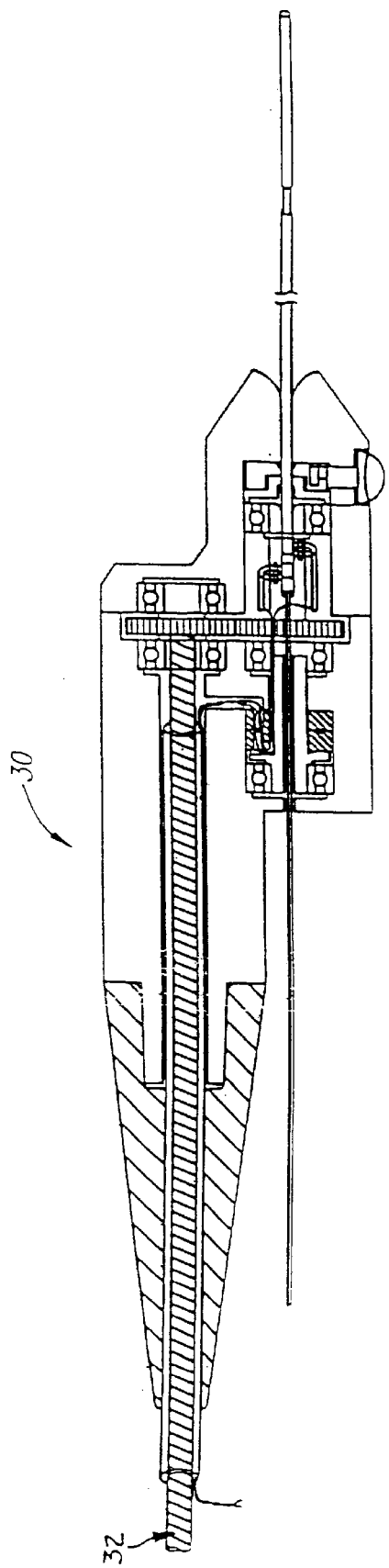
FIG. 7 shows a motor drive adapter which interfaces with an extension wire by offsetting the rotational axis of the extension wire.

Ultrasound imaging guidewire 10 includes an imaging guidewire body 12 which houses a rotatable transducer assembly 18, a static central core structure 20, a floppy tip assembly 14, a proximal connector 16 for disengaging the floppy tip 14 and static central core 20 from the imaging guidewire body 12, and electrical connectors 26 for coupling to a motor drive adapter 30 (shown in FIG. 7). The imaging guidewire body 12 has an outside diameter of approximately 0.035 inch. The overall length of ultrasonic guidewire 10 varies from approximately 40 cm to 300 cm.

The imaging guidewire is adapted for passage through a long, narrow body lumen such as a restricted, tortuous blood vessel. With ultrasound guidewire 10 inserted into a particular lumen of a patient's body, rotation of transducer assembly 18 by a motor drive adapter 30 connected to an ultrasound control system allows real-time, 360 degree ultrasonic images to be obtained of the body lumen. The control system processes data supplied by rotating transducer assembly 18 and displays real-time ultrasound images on a display device.

Imaging Guidewire Body

The imaging guidewire body 12 is formed from a substantially hollow tube designed to provide sufficient tensile strength and lateral stiffness to enable the guidewire 12 to maneuver a tortuous path. The body 12 also transmits torque to provide a substantially one-to-one correspondence between rotation of the proximal and distal ends of the tube to permit accurate imaging. As one skilled in the art would understand, the guidewire body 12 can be formed by a number of different materials including a metal alloy such as Nitinol or stainless steel. In an alternative embodiment, the imaging guidewire body 12 is a made of a composite material such as carbon fiber. In the preferred embodiment, a Nitinol hypotube is used because it minimizes kinking, transmits a high amount of torque, and is a memory metal that retains its shape after being bent. The imaging guidewire body 12 may have varying lengths from approximately 30 cm to 150 cm.

The imaging guidewire body 12 comprises an ultrasonic transducer assembly 18. As the transducer assembly 18 rotates, it provides 360 degree scanning of the lumen wall surrounding the transducer assembly 18. The transducer assembly 18 is adhesively bonded to the imaging guidewire body 12.

The transducer assembly 18 includes a piezoelectric crystal (PZT) with a matching layer on one side and a backing layer formed of acoustically absorbent material on the other side. The transducer assembly 18 in one embodiment maybe "air-backed" so as to increase the efficiency of the transducer. The ultrasound signal does not transmit through the air backing so therefore it is reflected entirely forward which increases the efficiency of the transducer. As one of skill in the art would understand, however, the transducer assembly 18 can be manufactured using alternate materials and designs.

At the proximal end of the imaging guidewire body 12, a pair of electrical connectors 26 are provided that couple a detachable motor drive adapter 30 (see FIG. 7) to a coaxial cable located inside the ultrasonic imaging guidewire 10. The coaxial cable includes an inner wire and an outer wire which are wrapped around each other. Proximal to the transducer assembly 18, the inner and outer wires are separated so that the inner wire is connected to the front of the transducer 18 and the outer wire is connected to the back of the transducer 18.

Figure 4A:
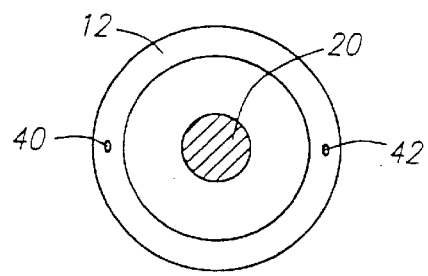
FIGS. 4A–4C depict alternative methods of adhering wires to the imaging guidewire body.
Figure 4B:
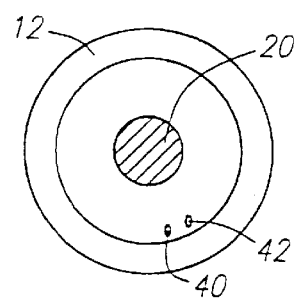
Figure 4C:
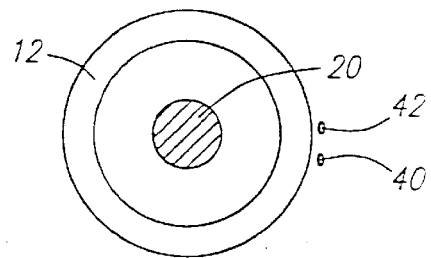

There are a number of alternative methods of adhering the wires to the imaging guidewire body. In one embodiment, shown in FIG. 4A, the wires 40, 42 are buried in the wall of the imaging guidewire body 12. In FIG. 4B, an alternate method of adhering the wires 40, 42 to the inside wall of the imaging guidewire body 12 is shown. The wires 40, 42 can be spread throughout the inside wall to eliminate any detrimental effects on uniform rotation of the guidewire body 12. In another embodiment shown in FIG. 4C, the wires 40, 42 are adhered to the outside wall of the imaging guidewire body 12. The wires may comprise flexleads which are flat and assist in meeting size constraints of the body 12. An adhesive may be added to the wires 40, 42 to prevent their movement or the interaction between the static central core 20 and the wires 40, 42. It should be noted that the orientation and placement of the wires 40, 42 is for exemplary purposes only. As one of ordinary skill in the art would understand, the wires 40, 42 can be placed anywhere around the circumference of the imaging guidewire body 12.

Static Central Core and Floppy Tip

The present invention comprises a static central core 20 occupying substantially the cross-section of the guidewire 10 throughout the imaging guidewire body 12 and distal of the transducer assembly 18. The static central core 20 is formed from stainless steel or Nitinol. This static central core 20 enhances lateral and axial stiffness, and minimizes the possibility of kinking of the imaging guidewire body 12.

The static central core 20 is welded to the floppy tip 14 which is radiopaque. In an alternative embodiment, only part of the floppy tip 14 is radiopaque. The floppy tip 14 is formed from a coil stacked upon itself that is soft and pliable so that it will minimize damage to the patient's vessels when it is being positioned in the patients body. Furthermore, the floppy tip 14 is formable so that the physician can reshape the distal tip to assist in maneuvering the imaging guidewire 10 through the patient's vessels. The floppy tip 14 is formed from a heavy metal such as gold, platinum or iridium.

In an alternative embodiment the static central core 20 is an extended version that permits over-the-wire catheter exchange. In another alternative embodiment, the extended static central core 20 has a connector to attach or detach additional length to or from the static central core 20.

Sheath Covering the Imaging Guidewire Body

When the imaging guidewire body 12 is positioned in certain areas of the body, such as the aorta, a sheath is needed to provide safety. The sheath 28 is designed with a preferably thin material because it is necessary to be able to obtain ultrasound images through the sheath 28. Additionally, the sheath 28 must be nonkinkable and sufficiently strong to be maneuvered through a patient's body.

Figure 5:
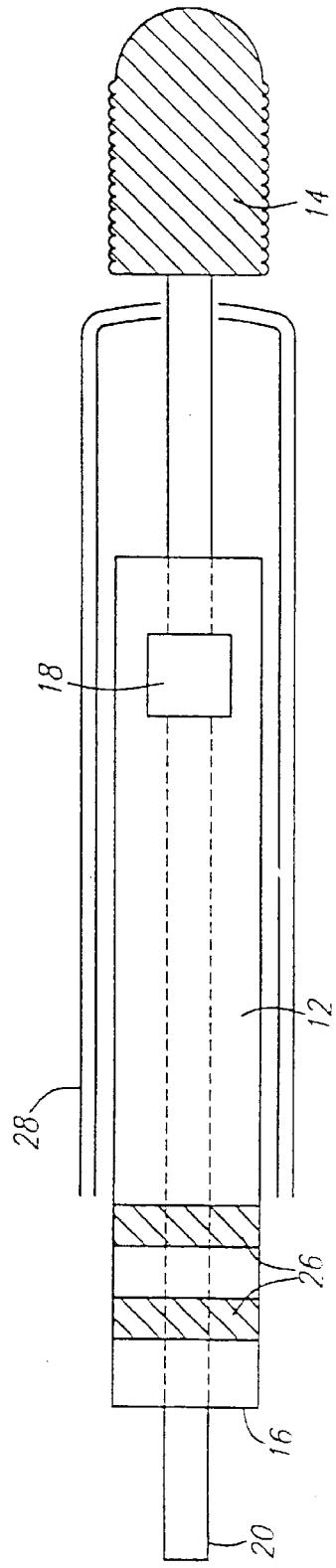
FIG. 5 is an elevational view of the ultrasound imaging guidewire with a sheath that does not translate axially with the imaging guidewire body.

If a sheath 28 is employed to surround the imaging guidewire body 12, a fluid such as blood or saline must be filled between the sheath 28 and the imaging guidewire body 12 to prevent air bubbles. It is desirable to eliminate air bubbles, because an air bubble will degrade the image quality. This is because the acoustical waves emitted from the transducer 18 do not travel through air. Therefore, a fluid that allows acoustical waves to be transmitted must be flushed into the sheath. As shown in FIG. 5, there is a gap between the imaging guidewire body 12 and the sheath 28, and thus that gap must be flushed with a fluid. There are a number of known fluid alternatives for filling the area between the sheath 28 and the body 12 including saline and blood. There are also alternative methods for inserting the fluid. One such method is to have apertures along the perimeter of the sheath 28 that permit fluid to enter the sheath 28 from the patient's body. Alternatively a fluid such as saline is inserted into the sheath 28 at the proximal end of the sheath 28, such as by a syringe. In another embodiment, a vacuum is created at the proximal end which causes the blood to be sucked up and into the desired area between the sheath 28 and the guidewire body 12. Alternatively, the fluid is distally filled into the sheath 28. Furthermore, to assist in any of these fluid flushing processes, a hydrophilic coating can be placed on both the inner and outer walls of the sheath which provides smoother fluid absorption. In one embodiment, the sheath 28 is covered with an anti-coagulant coating because blood clots may degrade the ultrasound image quality.

Figure 6:
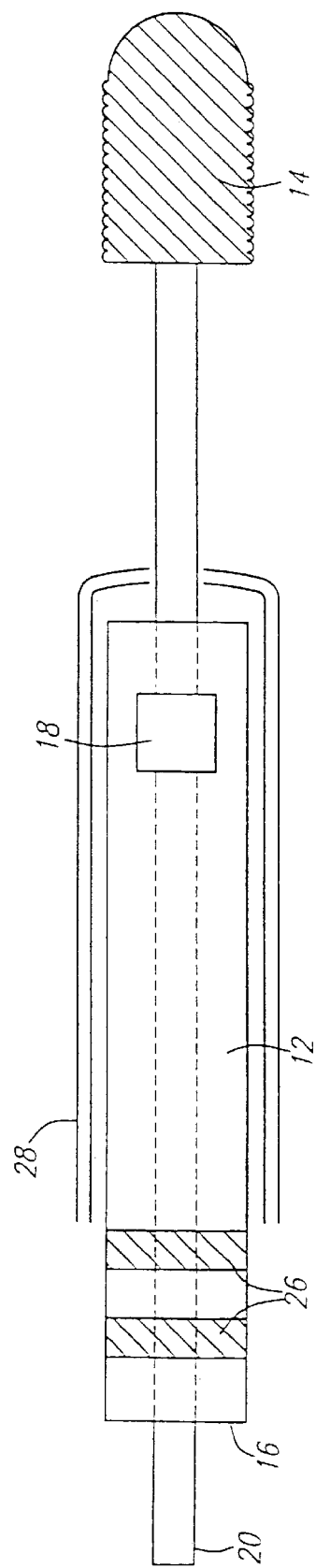
FIG. 6 is an elevational view of the ultrasound imaging guidewire with a sheath that does translate axially with the imaging guidewire body.

As shown in FIG. 5, in one embodiment, the sheath 28 stays in place, never rotating or translating axially. In another embodiment, as shown in FIG. 6, although the sheath 28 does not rotate, it does translate axially with the static central core 20. The proximal connector 16 establishes the lateral positioning of the sheath 28 and the imaging body 12.

The sheath 28 can be made of a number of different materials including polyethylene, silicon rubber or any acoustically transparent material. Optionally, for the embodiment of the sheath 28 that translates axially with the imaging body 12, the sheath may be made of a stronger material or reinforced with metal braids. The reinforced material is not placed opposite the transducer assembly 18 so as to not interfere with the transmission of acoustical waves from the transducer assembly 18. Also the material of the sheath 28 may be thinned out at the transducer position to permit an increase in transducer size (and therefore to permit better imaging).

Proximal Connector for Disengaging the Imaging Guidewire Body from the Static Central Core As shown in FIGS. 1A and 1B, the proximal connector 16 permits the imaging guidewire body 12 and its transducer assembly 18 to be disengaged from the floppy tip 14. When the transducer assembly 18 is disengaged from the floppy tip 14, as shown in FIG. 1B, the user can obtain acoustical images of the site or sites of interest while maintaining the proper guidewire position. The ability to disengage the transducer assembly 18 enables the user to easily obtain multi-position images of the patient's vessels or other sites of interest. The user may both advance and withdraw the detachable transducer assembly 18 during the real-time imaging to more accurately position transducer assembly 18 at the site of interest, e.g., a region stenosed with plaque. The proximal connector 16 is used to disengage the transducer assembly 18 from the floppy tip 14. A torquer can be used to hold the static central core 20 and the imaging body 12 together, as well as assisting the physician in turning or rotating the guidewire. Furthermore, in an alternative embodiment, the proximal connector 16 can be part of the motor drive adapter 30.

Figure 2A:
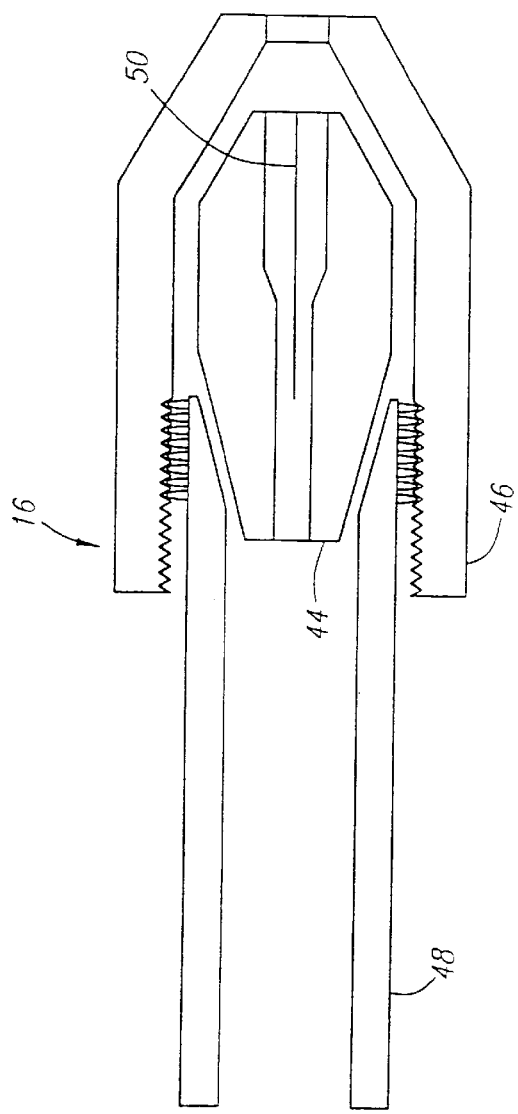
FIG. 2A shows a torquer.
Figure 2B:
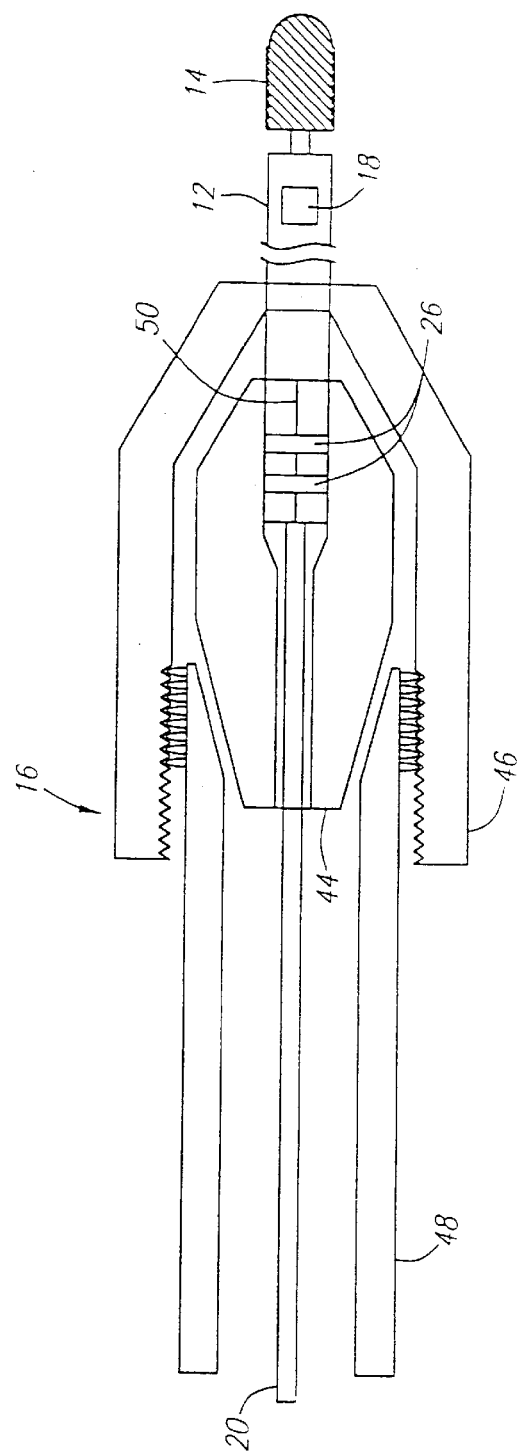
FIG. 2B shows a torquer with an imaging guidewire body and static central core.
Figure 3:
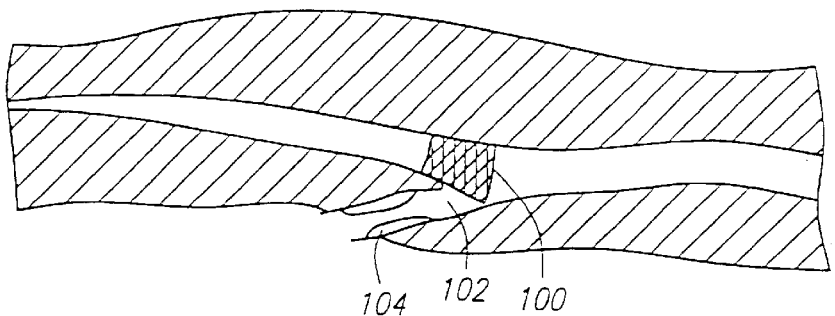
FIG. 3 is a cross-sectional view of a bifurcating blood vessel with a stent incorrectly placed causing "stent jail."

FIG. 2A shows the preferred embodiment of the proximal connector 16. One of ordinary skill in the art, however, would understand that the proximal connector 16 can be implemented with alternate designs. The proximal connector 16 includes a slotted collet 44. When the slotted collet 44 is uncompressed, the ultrasound imaging guidewire body 12 and static central core 20 are fed into the proximal connector 16, through the threaded collar 46 and into the slotted collet 44. When the slotted collet 44 is compressed, the imaging guidewire body 12 and static central core 20 are locked together to act as a standard guidewire, as shown in FIG. 2B. The slotted collet 44 is compressed by turning the threaded collar 46 which forces the slotted collet 44 into the tapered handle 48.

When compressed, the slotted collet 44 is shaped so as to tightly engage the guidewire body 12 and static central core 20. Hence, the compression of slotted collet 44 fixes the guidewire body's position relative to the static central core's position. The slotted collet 44 is also sized so that the static central core 20 passes entirely through the slotted collet 44, past the distal end of the tapered handle 48. Furthermore, the slotted collet 44 is sized so that the imaging guidewire body 12 is only partially inserted into the collet 44. When uncompressed, the slotted collet 44 is also sized such that the radial clearance is minimal between the imaging guidewire body 12 and its respective bore in the collet 44. Similarly, the slotted collet 44 is sized such that the radial clearance is minimal between the static central core 20 and its respective bore in the collet 44. In an alternative embodiment, the partial slot 50 of the collet 44 can be extended to the distal end of the collet 44 thereby creating a two-piece collet.

Connection Between the Motor Drive Unit and the Imaging Guidewire

At the most proximal portion of the imaging guidewire 10, a motor drive adapter 30 enables connection and subsequent disconnection of the ultrasonic imaging guidewire 10 to a motor drive unit for obtaining ultrasonic images. The motor drive unit adapter 30 has three primary goals, first to provide a sterile connection to the guidewire 10, second to provide a mechanical connection to the guidewire 10, and third to provide an electrical connection.

A problem is encountered when connecting the motor drive unit to the guidewire 10 because the motor drive unit is not sterile. Thus, if the guidewire 10 is plugged directly into the motor drive unit, then at least the sterility of the proximal end of the guidewire 10 is compromised. This is particularly a problem when the user performs a catheter exchange over the non-sterile proximal end of the guidewire 10. A solution is to have a disposable adapter which will interface with the non-sterile motor drive unit. Such a disposable motor drive adapter 30 is shown in FIG. 7. In the embodiment shown in FIG. 7, the entire device shown is sterile and preferably disposable. The motor drive adapter 30 includes an umbilical drive shaft 32 which makes it easier to couple the guidewire 10 and the motor drive unit. FIG. 7 permits an extension guidewire to be used because the motor drive adapter 30 has a hole at the proximal end where the extended portion of the extension guidewire is fed through. Furthermore, the extension guidewire 10 has its rotational axis offset from the rotational axis of the umbilical drive shaft 32 which is connected to the motor drive unit.

One skilled in the art would understand that numerous methods can be employed to create a mechanical connection. The mechanical connection needs to provide a firm grip on the rotating guidewire 10 so that there will be no slippage. The mechanical connection also needs to insure that the rotation from the motor drive adapter is transmitted smoothly to the guidewire 10, so that the guidewire 10 rotates smoothly. In one embodiment, there is a physical depression at one end of the motor drive adapter 30. Once the motor drive adapter engages the guidewire 10, it forces the guidewire 10 to rotate. Alternatively the motor drive adapter 30 does not have a physical depression, but engages the guidewire 10 with sufficient tightness to ensure that the guidewire 10 rotates smoothly. In another embodiment, two rubber wheels surround the guidewire 10. One rubber wheel is rotated in one direction, while the second rubber wheel is rotated in another direction. Meanwhile the imaging guidewire 10 spins in between the two rubber wheels. In the preferred embodiment, a multi-leaved spring arrangement is used to provide a mechanical connection between the guidewire 10 and the motor drive adapter 30.

An electrical connection that allows ultrasonic energy to be transmitted from motor drive adapter 30 to the wires 40, 42 inside the guidewire body 12 is provided by electrical connectors 26. In one embodiment, the electrical connectors 26 are formed by gold bands that are coupled to the motor drive adapter 30. The electrical connection aspect of the motor drive adapter 30 can be implemented using many different techniques, as one of skill in the art would understand. One method is to have a slipping contact that rubs on the rotating guidewire 10.

Another method uses electrodes on the rubber-wheel embodiment. In the preferred embodiment, non-slipping contacts with a rotary transformer are used.

The motor drive unit adapter 30 can be in a number of different forms including hollow, where the guidewire 10 is end loaded. In the preferred embodiment, the motor drive unit adapter 30 is clam-shelled shaped, so that the guidewire 10 can be side loaded. The side-loaded version is the preferred embodiment because it obviates the need to thread the guidewire 10 in and out and therefore makes it easier to load and unload.

While a presently-preferred embodiment of the invention has been disclosed, it will be obvious to those skilled in the art that numerous changes may be made without departing from the spirit or scope of the invention. It is intended that all matter contained in the above description or shown in the accompanying drawings shall be interpreted as being illustrative and not limiting. The invention, therefore, is not to be limited except in accordance with the below claims.

What is claimed is:

1. A medical guidewire adapted for insertion into a body, the guidewire comprising:

a guidewire body having a lumen;

a central core provided within the lumen of the guidewire body;

a diagnostic device coupled electrically to the central core; and a coupler adapted to selectively couple the guidewire body to the central core and to permit the axial translation of the guidewire body without axial translation of the central core.

2. The guidewire of claim 1 wherein the coupler, when disengaged, permits the axial translation of the guidewire body without axial translation of the central core.

3. The guidewire of claim 1 wherein the coupler, when engaged, permits the axial translation of the central core when the guidewire body is axially translated.

4. The guidewire of claim 1 further comprising a floppy tip at the distal end of the guidewire body, wherein the coupler, when engaged, permits the axial translation of the floppy tip when the guidewire body is axially translated.

5. The guidewire of claim 4 wherein the coupler, when disengaged, permits the axial translation of the guidewire body without axial translation of the floppy tip.

6. The guidewire of claim 1 wherein the diagnostic device is an imaging device.

7. The guidewire of claim 1 wherein the imaging device includes an ultrasound transducer.

8. The guidewire of claim 1 further comprising a motor drive adapter for connecting the central core to a motor drive unit.

9. The guidewire of claim 8 wherein the motor drive adapter further comprises an electrical connector.

10. The guidewire of claim 8 wherein the motor drive adapter further comprises a mechanical connector.

11. The guidewire of claim 9 wherein the electrical connector is a rotary transformer.

12. The guidewire of claim 10 wherein the mechanical connector comprises a rubber wheel.

13. The guidewire of claim 12 wherein the rubber wheel comprise electrodes.

14. The guidewire of claim 12 wherein the mechanical connector comprises a multi-leaved spring.

15. The guidewire of claim 1 further comprising a sheath connected to the guidewire body.

16. The guidewire of claim 15 wherein the sheath is axially translated with the guidewire body.

17. The guidewire of claim 15 wherein the sheath remains in place with the central core when the guidewire body is axially translated.

18. The guidewire of claim 15 wherein the diagnostic device includes an acoustical transducer and a fluid is flushed in the sheath to permit acoustical waves to transmit from the acoustical transducer.

19. The guidewire of claim 1 wherein the central core is static.

20. The guidewire of claim 1 further comprising:

a central core extension;

a coupler to selectively couple the central core extension to the central core.

21. The method of claim 1 wherein the steps of using the diagnostic device at the first, second and third sites of interest obtain an image at the first, second and third sites of interest.

22. A method of diagnosing within a body, the method comprising the steps of:

inserting a guidewire having an guidewire body and a central core into a first site of interest in a patient's body, the guidewire body having a central axis along the length of the guidewire body and a diagnostic device engaged to the central core with a coupler;

using the diagnostic device to assist diagnosis at the first site of interest;

disengaging the coupler to separate the diagnostic device from the central core;

selectively coupling a central core extension to the central core;

translating the guidewire body of the guidewire along the axis of the guidewire body to a second site of interest without axially translating the central core; and using the diagnostic device to assist diagnosis at the second site of interest.

23. The method of claim 22 wherein the step of using the diagnostic device at the first site of interest obtains an image at the first site of interest.

24. The method of claim 22 further comprising the steps of:

selectively decoupling the central core extension from the central core;

translating the guidewire body of the guidewire along the axis of the guidewire body to a third site of interest without axially translating the central core; and using the diagnostic device to assist diagnosis at the third site of interest.

25. The method of claim 23 wherein the step of using the diagnostic device to obtain an image at the first site of interest rotates the diagnostic device.

26. The method of claim 22 wherein the steps of using the diagnostic device at the first and second sites of interest obtains images at the first and second sites of interest.

27. The method of claim 26 wherein the steps of using the diagnostic device to obtain images at the first and second sites of interest rotate the diagnostic device.

28. The method of claim 22 further comprising treating a portion of the body.

29. The method of claim 28 wherein the treating step includes placing a stent within the body.

30. The method of claim 28 wherein the treating step includes inflating a balloon within the body.

31. The method of claim 29 further comprising after the stent placing step, the steps of:

translating the guidewire body of the guidewire along the axis of the guidewire body to a third site of interest without axially translating the central core; and using the diagnostic device to assist diagnosis of a third site of interest.

32. The method of claim 30 wherein the step of using the diagnostic device to assist diagnosis of the third site of interest obtains an image at the third site of interest.

33. The method of claim 30 further comprising after the balloon inflating step, the steps of:

translating the guidewire body of the guidewire along the axis of the guidewire body to a third site of interest without axially translating the central core; and using the diagnostic device to assist diagnosis of a third site of interest.

34. The method of claim 33 wherein the step of using the diagnostic device to assist diagnosis of the third site of interest obtains an image at the third site of interest.

35. The method of claim 22 wherein the step of using the diagnostic device at the first site of interest is performed after the step of coupling the central core extension to the central core.

36. The method of claim 22 wherein the translating step is performed before the step of coupling the central core extension to the central core.

37. The method of claim 22 wherein the step of using the diagnostic device at the first site of interest emits acoustical energy to obtain an image at the first site of interest.

* * * * *